United States Patent [19]

Lin et al.

[11] Patent Number: 4,536,604
[45] Date of Patent: Aug. 20, 1985

[54] BUTADIENE REDUCTIVE DIMERIZATION USING A PLATINUM CATALYST AND POLYMERIC AMINE PROMOTER

[75] Inventors: Jiang-Jen Lin, Round Rock; David C. Alexander, Austin, both of Tex.

[73] Assignee: Texaco Inc., White Plains, N.Y.

[21] Appl. No.: 589,805

[22] Filed: Mar. 15, 1984

[51] Int. Cl.$^3$ .................. C07C 2/76; C07C 11/00
[52] U.S. Cl. .................. 585/601; 585/608
[58] Field of Search .................. 585/601

[56] References Cited

U.S. PATENT DOCUMENTS

| | | | |
|---|---|---|---|
| 3,013,066 | 12/1961 | Alderson | 585/601 |
| 3,388,182 | 6/1968 | Tinsley | 585/601 |
| 3,562,351 | 2/1971 | Mertzweiller et al. | 585/511 |
| 3,565,821 | 2/1971 | Su | 502/32 |
| 3,732,326 | 5/1973 | Chen | 585/820 |
| 3,823,199 | 7/1974 | Wright | 585/506 |
| 3,848,015 | 11/1974 | Wilke | 585/16 |
| 3,917,730 | 11/1975 | Tkatchenko | 585/511 |
| 3,920,763 | 11/1975 | Yoo | 585/509 |
| 3,925,497 | 12/1975 | Josey et al. | 585/511 |
| 4,229,606 | 11/1980 | Nozaki | 585/506 |
| 4,243,829 | 1/1981 | Pittman, Jr. et al. | 585/601 |
| 4,334,117 | 6/1982 | Yoshimura et al. | 585/509 |
| 4,377,719 | 3/1983 | Pittman, Jr. et al. | 585/509 |

FOREIGN PATENT DOCUMENTS

| | | | |
|---|---|---|---|
| 2050774 | 10/1969 | Fed. Rep. of Germany | 585/506 |
| 7426 | 1/1982 | Japan | 585/601 |
| 1341324 | 12/1973 | United Kingdom | 585/506 |

OTHER PUBLICATIONS

J. Org. Chem., 1981 vol. 46 (2356–2362) Selective Telomerization of Butadiene with Various Nucleophiles Catalyzed by Polymer-Bound Palladium(10) Complexes.

*Primary Examiner*—D. E. Gantz
*Assistant Examiner*—Helane Myers
*Attorney, Agent, or Firm*—Jack H. Park; David L. Mossman; Cynthia L. Kendrick

[57] ABSTRACT

A method for preparing 1,6-octadiene by reacting 1,3-butadiene with formic acid in the presence of a platinum(II) catalyst and a polymeric tertiary amine catalyst is described. The combination of a platinum(II) catalyst such as platinum acetylacetonate with a polymeric tertiary amine promoter such as AMBERLYST ® A21 macroreticular ion-exchange resin gives a high selectivity to 1,6-octadiene as opposed to the 1,7-octadiene form. A reaction temperature between 50° and 150° C. is preferred, and carbon dioxide and a solvent may also be employed.

18 Claims, No Drawings

BUTADIENE REDUCTIVE DIMERIZATION USING A PLATINUM CATALYST AND POLYMERIC AMINE PROMOTER

CROSS-REFERENCE TO RELATED APPLICATION

This application is related to U.S. patent application Ser. No. 589,804 which concerns the dimerization/hydroformylation of butadiene with formic acid over a platinum catalyst with no polymeric amine promoter to give 2,7-octadienyl formate, filed of even date.

BACKGROUND OF THE INVENTION

1. Field of the Invention

The invention relates to the preparation of 1,6-octadiene by the reductive dimerization of 1,3-butadiene with formic acid and more particularly relates to such a process conducted in the presence of a platinum catalyst and a solid polymeric amine promoter.

2. Other Processes in the Field of the Invention

Linear dimerization of butadiene (1,3-butadiene) provides a source of $C_8$ unsaturated hydrocarbon intermediates useful for the synthesis of diacids, diesters, diols or diamines. Linear oligomerization of butadiene typically results in the formation of n-octatriene products, and in particular either 1,3,6-octatriene or 1,3,7-octatriene. Unfortunately, such compounds are unreactive in many reactions or give complex reaction mixtures. 1,7-Octadiene is also a common product. However, 1,6-octadiene is another typical product. It may be used in the production of decanediol or 1,7-octadiene. A typical problem in these dimerization methods is that a variety of products are produced. It is desirable to discover systems which yield primarily one substance.

The dimerization of olefins is a well known reaction. U.S. Pat. No. 3,562,351 describes a method for dimerizing and co-dimerizing monoolefins in the presence of a Group VIII water-soluble metal salt which is activated by treatment with an organometallic compound. The Group VIII metal is preferably nickel, cobalt or mixtures thereof. A rhodium catalyst is useful in synthesizing dienes from alphamonoolefins and conjugated dienes according to U.S. Pat. No. 3,565,821. Further, U.S. Pat. No. 3,848,015 teaches the production of dimers and trimers using a carbonyl moiety-free complex of a transition metal of Group VIII and an electron donor. The Group VIII transition metal is listed as being iron, cobalt, nickel, ruthenium, rhodium, palladium, osmium, iridium and platinum, although the preferred metals therein are iron, cobalt and nickel, nickel being especially preferred. Dimerization of diolefins may also be effected by maintaining the olefins in inert solvent solution in contact with a catalyst which is the product of the interaction between two metal complexes, each of which is a nitrosyl and/or carbonyl ligand, as seen in U.S. Pat. No. 3,917,730.

A general review of butadiene telomerization is given by R. Baker in "$\pi$-Allylmetal Derivatives in Organic Synthesis", *Chemical Reviews,* Vol. 73 (1973), No. 5, pp. 491–493. Transition metal catalysts mentioned therein include triallyl cobalt, $Co_2(CO)_8$, cobalt(II) chloride, cobalt acetylacetonate, ferric acetylacetonate, ferric chloride, nickel chloride, $\pi$-allylpalladium chloride and $(Ph_3P)_2Pd$ (maleic anhydride)$_2$. Tetrakis(triphenylphosphine)platinum is also mentioned as yielding mainly vinyl cyclohexene from the dimerization of butadiene in benzene solution.

Palladium catalysts are particularly popular for the co-dimerization of 1,3-butadiene and ethylene. U.S. Pat. No. 3,920,763 employs a $\pi$-allyl complex catalyst for this purpose which comprises a palladium source, a monotertiary phosphine electron donor ligand, a combination reducing agent and Lewis acid and an acidic, solid, silica-based support material. A dienophile-coordinated palladium-phosphine complex such as bis-(triphenylphosphine)-(maleic anhydride) palladium is the preferred catalyst for co-dimerization and homo-dimerization of butadienes in U.S. Pat. No. 3,925,497.

European patent application No. 0004408 teaches the preparation of 1,7-octadiene by the hydrodimerization of butadiene using a palladium-organophosphine catalyst which has been pre-treated with a reducing agent. The reducing agent may be formic acid, the triethylamine salt of formic acid, hydrazine, hydrogen or carbon monoxide. Palladium acetylacetonate is mentioned as a suitable palladium catalyst. Amine solvents may be used and carbon dioxide is taught as being able to increase the butadiene conversion. Two recent patents to Pittman, U.S. Pat. Nos. 4,243,829 and 4,377,719, and *J. Mol. Cat.,* Vol. 15 (1982), pp. 377–381 reveal processes for preparing 1,7-octadiene selectively by dimerizing butadiene in the presence of a catalytic amount of palladium and a tertiary phosphine including a solvent, a strong base and formic acid.

Certain platinum catalysts have also been shown to be useful in butadiene dimerizations. L. H. Slaugh, et al. in "A Novel Effect of Carbon Dioxide on Catalyst Properties. Dimerization of Butadiene", *Journal of the American Chemical Society,* Vol. 91, No. 21 (1969), pp. 5904–5, disclose that the presence of carbon dioxide enhances the yield to 1,3,7-octatriene over platinum, palladium and nickel catalysts. The metals are complexed with triphenyl phosphines and occasionally carbonyls. Platinum catalysts such as lithium tetrachloroplatinate(II) and $Pt(C_5H_7O_2)_2$ are used to make 1,7-octadiene from butadiene in the presence of dimethylformamide and formic acid as described in S. Gardner, et al., "Platinum-Metal Catalyzed Formation of Linear Octadienes", *Tetrahedron Letters,* No. 2 (1972), pp. 163–164. However, the selectivity to 1,6-octadiene is unsatisfactory.

U.S. Pat. No. 3,732,328 teaches the production of an octadiene selected from the group consisting of octa-1,6-diene, octa-1,7-diene, monomethylocta-1,6-diene, monomethylocta-1,7-diene, dimethylocta-1,6-diene and dimethylocta-1,7-diene. Butadiene and/or isoprene at a temperature of 20° to 200° C. is contacted with a $10^{-1}$ to $10^{-5}$ molar concentration of a platinum, palladium or ruthenium catalyst, such as halides, alkanoates, acetylacetonates, bisbenzonitrile palladium(II) and lithium palladous chloride. Formic acid and a polar solvent must also be present. Dimethyl formamide is a preferred solvent. However, this process suffers from a low yield to 1,6-octadiene.

Similarly, U.S. Pat. No. 3,823,199 teaches that 1,6- and/or 1,7-octadienes may be produced by reacting 1,3-butadiene with metallic platinum, palladium, rhodium, ruthenium or osmium in the presence of formic acid. Preferably, a compound of one or more of these catalysts in a non-polar solvent such as benzene is employed. Selectivities to 1,6-octadiene are not disclosed, and no amine promoter is used.

S. Teranishi in *J. Org. Chem.*, Vol. 46 (1981), pp. 2356–2362, discloses a palladium(O) complex supported on a phosphinated polystyrene as a catalyst for the reaction of 1,3-butadiene and formic acid. In this case, 1,7-octadiene was produced exclusively.

Finally, U.S. Pat. No. 4,334,117 reveals an improved process for the preparation of alkadienes by contacting butadiene or isoprene with a platinum or palladium catalyst, optionally in a sulfolane solution, in the presence of a tertiary lower alkylamine formate and at least one particularly-defined phosphine compound. Platinum acetylacetonate is specifically mentioned.

Given the methods noted above, it would still be desirable to discover a process providing high selectivity to 1,6-octadiene with ease of subsequent separation.

SUMMARY OF THE INVENTION

The invention concerns a method for preparing 1,6-octadiene by reacting 1,3-butadiene with formic acid in the presence of a platinum catalyst and a polymeric tertiary amine promoter.

DETAILED DESCRIPTION OF THE PREFERRED EMBODIMENTS

The reaction of this invention may be stoichiometrically diagrammed as follows

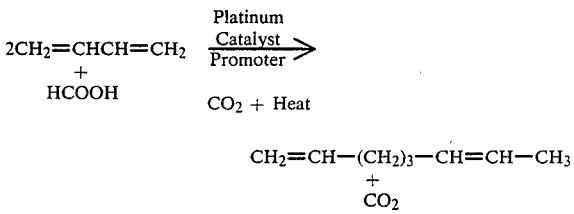

$$CH_2=CH-(CH_2)_3-CH=CH-CH_3$$
$$+$$
$$CO_2$$

It may be seen that two moles of 1,3-butadiene should be used for every mole of formic acid. The molar ratio of butadiene to formic acid should range from 5:1 to 1:5, preferably. In practice, a slight excess of 1,3-butadiene is preferred. Surprisingly, the predominant product is 1,6-octadiene in contrast to 1,7-octadiene.

The catalyst should be a platinum catalyst, preferably a platinum(II) catalyst. Various possible platinum(II) catalysts include $PtCl_2$, $PtBr_2$, $(PhCN)_2PtCl_2$, $(Ph_3P)_2PtCl_2$. Ligand stabilized Pt(O) compounds such as $(Ph_3P)_4Pt$ might also be found to be useful. In these formulas, Ph designates a phenyl group. The most preferred catalyst is platinum acetylacetonate abbreviated $Pt(acac)_2$. The molar ratio of butadiene reactant to platinum catalyst is preferably 10,000:1 to 1000:1.

A novel feature of the instant invention is the use of an amine promoter along with the platinum catalyst. The amine promoter should be a polymeric tertiary amine; that is, when polymerized the amine nitrogens should be tertiarily substituted. Polymeric amines and amides which may be used include polyamide resins, poly(vinylpyridine), polyvinylpyrrolidone and dimethylamino polymers. The preferred polymeric tertiary amine polymer is the poly(styrene-dimethylamine). These types of amine polymers can be acquired as macroreticular ion-exchange resins sold as AMBERLYST-®A21 resins by Rohm and Haas Company. Other possible amine promoters are the tertiary amine polymer forms of morpholine, piperidine, pyrrolidine, diphenylamine and diethylamine. Polystyrene-supported benzyltrimethylammonium resins may also prove suitable. The weight ratio of butadiene reactant to amine promoter is preferably 1:1 to 100:1, although the most preferred weight ratio is about 10:1.

The preferred reaction temperature is 50° to 150° C. with an especially preferred temperature of about 100° C. Although carbon dioxide is not essential to the reaction, its presence is preferred. A $CO_2$ partial pressure of about 50 to 500 psi is preferred.

A solvent may also be present to help facilitate the reaction. Any organic solvent such as alcohols and esters may be used, but aprotic, polar or non-polar solvents are preferred. Such preferred solvents include oxygenates such as tetrahydrofuran (THF) and other ethers and aromatics such as toluene, chlorobenzene, nitrobenzene, benzonitrile and the like.

The use of the polymeric amine for this reaction affords two significant features. First, there is a high selectivity toward 1,6-octadiene formation; in some cases a mole ratio of greater than 90:10 molar ratio of 1,6- to 1,7-octadiene is achieved. Secondly, there is great ease in separating the desired product from the solid amine. It is suggested that decantation or filtration procedures be used for separation. In addition, 4-vinylcyclohexene has been observed as a minor side product. Octadienes are useful in various polymer syntheses and in the syntheses of diacids, diesters, diols and diamines.

The invention will be further illustrated by the following experimental examples. These examples are not intended to limit the invention beyond the spirit and scope thereof defined in the appended claims. It is expected that one skilled in the art could modify the invention in terms of changing catalyst/promoter types and proportions, temperatures and pressures outside these specific examples but still remain within the spirit and scope of the claims.

EXAMPLE 1

To a 300 ml stainless steel magnedrive reactor were charged platinum(II) acetylacetonate (0.039 g, 0.1 mm), formic acid (12.0 g, 0.26M), solid AMBERLYST-®A21 (10.0 g) and THF (6.0 g). The reactor was sealed and purged of air by carbon dioxide. Then, butadiene (about 32 g, 0.6M) was pressured into the reactor along with pure $CO_2$ to the pressure of 120 psi. The system was heated to 100°–120° C. and maintained at this temperature range for 4 hours reaction time. The maximum pressure of 500 psi was observed during the reaction process. At the end of the reaction, the reactor was allowed to cool to room temperature. A light yellow, clear product solution was obtained (31.0 g) by decantation or filtering off the solid AMBERLYST A21. Among the 31.0 g liquid, the top layer (29.0 g) was analyzed by gas-liquid chromatography and showed the following results:

| | |
|---|---|
| Butadiene, % | 23 |
| THF, % | 21 |
| 1,7-octadiene, % | 1.8 |
| 1,6-octadiene, % | 29 |
| 4-vinylcyclohexene, % | 25 |

The product selectivities were estimated to be: 52% 1,6-octadiene, 3% 1,7-octadiene and 45% 4-vinylcyclohexene.

EXAMPLES 2–7

Examples 2–7 were conducted as in Example 1. Conditions and results are presented in Table I. For comparison, Table II has also shown the relative product ratio of 1,6- to 1,7-octadiene and the catalyst efficiency in one unit of g-(1,6- +1,7-octadiene)/g-atm-platinum/hr.

TABLE I 1,6-Octadiene Synthesis via Butadiene Dimerization

| Example | Catalyst | Formic Acid | Amine Used | Solvent Used | Butadiene Charged | Initial & Max. CO$_2$ Pressure | Reaction Temp, °C. | Reaction Time | Product Selectivity, % | | | |
|---|---|---|---|---|---|---|---|---|---|---|---|---|
| | | | | | | | | | 1,6-Octadiene | 1,7-Octadiene | 4-vinyl-cyclohexene | Others, % |
| 1 | Pt(acac)$_2$ (0.1 mm) (0.039 g) | 12.0 g (0.26 M) | AMBERLYST® A-21 (10.0 g) | THF (6.0 g) | 32 g | 120–500 psi | 100–120 | 4 hrs. | 52 (76 mm) | 3 (4.7 mm) | 45 | 0 |
| 2 | Pt(acac)$_2$ (0.1 mm) (0.039 g) | 12.0 g (0.26 M) | None | THF (6.0 g) | 45 g | 100–420 psi | 100–120 | 1.5 hrs | 36 (49 mm) | 5 (7.2 mm) | 31 | 28 |
| 3 | Pt(acac)$_2$ (0.1 mm) (0.039 g) | None | None | THF (6.0 g) | 32 g | 100–415 psi | 100–130 | 4 hrs | trace | trace | ~100 (50 mm) | 0 |
| 4 | Pt(acac)$_2$ (0.1 mm) (0.039 g) | 12.0 g (0.26 M) | AMBERLYST A21 (5.0 g) | THF (6.0 g) | 21 g | 150–465 psi | 120 | 2 hrs | 58 (30 mm) | 6 (3 mm) | 36 | |
| 5 | Pt(acac)$_2$ (0.1 mm) (0.039 g) | 12.0 g (0.26 M) | AMBERLYST A21 (5.0 g) | THF (12.0 g) | 21 g | 110–340 psi | 110 | 5.5 hrs | 59 (34 mm) | 4 (2 mm) | 32 | 5 |
| 6 | Pt(acac)$_2$ (0.1 mm) (0.039 g) | 12.0 g (0.26 M) | 1 | THF (12.0 g) | 23 g | 100–335 psi | 110–118 | 5.5 hrs | 56 (48 mm) | 7 (6 mm) | 36 | 0 |
| 7[2] | Pt(acac)$_2$ (0.1 mm) (0.039 g) | 12.0 g (0.26 M) | DMF (0.25 m) | — | 32.4 g | — | 100 | 3 hrs | (58 mm) | (42 mm) | — | — |

[1]AMBERLYST A21 was recovered from run of Example 5 by filtering off the liquid.
[2]This example was taken from Tetrahedron Letters, pp. 163–164 (1972) for the purpose of comparison.

TABLE II

| Examples | 1 | 2 | 3 | 4 | 5 | 6 | 7 |
|---|---|---|---|---|---|---|---|
| Relative ratio of 1,6- to 1,7-octadiene | 93:7 | 87:13 | — | 91:9 | 94:6 | 88:12 | 58:42 |
| Catalyst Turnover (g octadiene/ g-atm Pt/ hr) | 22,000 | 41,000 | 0 | 18,000 | 6,500 | 11,000 | 37,000 |

A number of observations may be seen from the examples. In Example 3 where no formic acid was used only trace amounts of either octadiene were formed, all of the product essentially being 4-vinyl-cyclohexene. The make of 1,6-octadiene was reduced when no polymeric amine (AMBERYST A21) was employed (Example 2, only 36% selectivity to 1,6-octadiene). Comparative Example 7 using a prior art method was not as selective as the inventive technique in that substantial amounts of 1,7-octadiene were produced.

Another advantage of using polymeric amine is demonstrated in Examples 5 and 6 showing the reuse of AMBERYST A21 recovered from a convenient filtration procedure.

We claim:

1. A method for the preparation of 1,6-octadiene comprising
    reacting 1,3-butadiene with formic acid in the presence of a platinum(II) catalyst and a polymeric tertiary amine promoter.
2. The method of claim 1 in which the mole ratio of butadiene to formic acid is from about 5:1 to 1:5.
3. The method of claim 1 in which the platinum catalyst is platinum acetylacetonate.
4. The method of claim 1 in which the mole ratio of butadiene to platinum catalyst ranges from 10,000:1 to 1,000:1.
5. The method of claim 1 in which the amine promoter is selected from the group consisting of poly(dimethylamine), polyamide, poly(vinylpyridine) and polyvinylpyrrolidone solid, polymeric tertiary amines.
6. The method of claim 1 in which the weight ratio of butadiene to polymeric tertiary amine promoter ranges from 1:1 to 100:1.
7. The method of claim 1 in which carbon dioxide is present during the reaction.
8. The method of claim 1 in which the reaction is conducted at a temperature in the range between about 50° and 150° C. and at a CO$_2$ partial pressure between about 50 and 500 psi.
9. The method of claim 1 in which a solvent is employed which is selected from the group consisting of oxygenate solvents and aromatic solvents.
10. A method for the preparation of 1,6-octadiene comprising
    reacting 1,3-butadiene with formic acid in the presence of a platinum(II) acetylacetonate catalyst and a polymeric dimethylamine promoter.
11. The method of claim 10 in which the mole ratio of butadiene to formic acid is about 5:1 to 1:5.
12. The method of claim 10 in which the mole ratio of butadiene to platinum catalyst ranges from 10,000:1 to 1,000:1.
13. The method of claim 10 in which the weight ratio of butadiene to amine promoter ranges from 1:1 to 100:1.
14. The method of claim 10 in which carbon dioxide is present during the reaction.
15. The method of claim 10 in which the reaction is conducted at a temperature in the range between about 50° and 150° C. and at a CO$_2$ partial pressure between about 50 and 500 psi.
16. The method of claim 10 in which a solvent is employed which is selected from the group consisting of oxygenate solvents and aromatic solvents.

17. A method for the preparation of 1,6-octadiene comprising
reacting 1,3-butadiene with formic acid at a mole ratio of butadiene to formic acid of from 5:1 to 1:5 in the presence of a platinum(II) acetylacetonate catalyst and a polymeric amine promoter at a temperature in the range between 50° and 150° C. and at a $CO_2$ partial pressure between about 50 and 500 psi where the mole ratio of butadiene to platinum catalyst ranges from 10,000:1 to 1,000:1 and the weight ratio of butadiene to polymeric tertiary amine promoter ranges from 1:1 to 100:1.

18. The method of claim 17 in which a solvent is employed which is selected from the group consisting of oxygenate solvents and aromatic solvents.

* * * * *